United States Patent
Feige et al.

(10) Patent No.: US 12,317,914 B2
(45) Date of Patent: *Jun. 3, 2025

(54) COMPOSITIONS AND METHODS USING ONE OR MORE AUTOPHAGY-INDUCING AMINO ACIDS TO POTENTIATE MUSCULOSKELETAL EFFECT OF ONE OR MORE ANABOLIC AMINO ACIDS

(71) Applicant: SOCIETE DES PRODUITS NESTLE S.A., Vevey (CH)

(72) Inventors: Jerome Feige, Crissier (CH); Philipp Gut, Geneva (CH); Gabriele Civiletto, Lausanne (CH); Claire Boutry, Villars Burquin (CH)

(73) Assignee: Societe des Produits Nestle S.A., Vevey (CH)

( * ) Notice: Subject to any disclaimer, the term of this patent is extended or adjusted under 35 U.S.C. 154(b) by 762 days.

This patent is subject to a terminal disclaimer.

(21) Appl. No.: 17/596,144

(22) PCT Filed: Jun. 4, 2020

(86) PCT No.: PCT/EP2020/065534
§ 371 (c)(1),
(2) Date: Dec. 3, 2021

(87) PCT Pub. No.: WO2020/245299
PCT Pub. Date: Dec. 10, 2020

(65) Prior Publication Data
US 2022/0295854 A1   Sep. 22, 2022

Related U.S. Application Data

(60) Provisional application No. 62/858,496, filed on Jun. 7, 2019.

(51) Int. Cl.
| | |
|---|---|
| *A23L 33/175* | (2016.01) |
| *A23L 33/18* | (2016.01) |
| *A61K 9/14* | (2006.01) |
| *A61K 31/198* | (2006.01) |
| *A61K 38/01* | (2006.01) |
| *A61P 3/02* | (2006.01) |
| *A61P 21/00* | (2006.01) |

(52) U.S. Cl.
CPC .............. *A23L 33/175* (2016.08); *A23L 33/18* (2016.08); *A61K 9/14* (2013.01); *A61K 31/198* (2013.01); *A61K 38/011* (2013.01); *A61K 38/018* (2013.01); *A61P 3/02* (2018.01); *A61P 21/00* (2018.01)

(58) Field of Classification Search
CPC ...... A23L 33/175; A23L 33/18; A23L 33/185; A23L 33/19; A61K 9/14; A61K 31/198; A61K 38/011; A61K 38/018; A61K 38/00; A61P 3/02; A61P 21/00
See application file for complete search history.

(56) References Cited

U.S. PATENT DOCUMENTS

| | | | |
|---|---|---|---|
| 9,597,367 B2* | 3/2017 | Wolfe | A61K 31/202 |
| 10,045,999 B2* | 8/2018 | Jourdan | A23L 33/155 |
| 2013/0090297 A1 | 4/2013 | Troup et al. | |
| 2014/0315788 A1 | 10/2014 | Wolfe et al. | |
| 2014/0343112 A1 | 11/2014 | Ferrando et al. | |
| 2014/0357576 A1 | 12/2014 | Breuille et al. | |
| 2015/0290223 A1 | 10/2015 | Jourdan et al. | |
| 2016/0339078 A1 | 11/2016 | Hamill et al. | |
| 2017/0027897 A1 | 2/2017 | Wang et al. | |

FOREIGN PATENT DOCUMENTS

| | | |
|---|---|---|
| EP | 2036552 | 3/2009 |
| EP | 2705844 | 3/2014 |
| JP | 2008534599 A | 8/2008 |
| WO | 2010108016 | 9/2010 |
| WO | 2018091564 | 5/2018 |
| WO | 2018118957 A1 | 6/2018 |
| WO | 2019090061 | 5/2019 |

OTHER PUBLICATIONS

Kelly et al. "8—Improving the sensory quality, shelf-life and functionality of milk" in: Functional and Speciality Beverage Technology, (CRC Press, 2009), p. 170-231. (Year: 2009).*
Carroll et al. (Amino Acids, 2015, 47, 2065-2088) (Year: 2015).*
Japanese Office Action for Appl No. 2021-567895 dated Jun. 18, 2024, 8 pages.

* cited by examiner

*Primary Examiner* — Layla D Berry
*Assistant Examiner* — Sarah Grace Scrivener
(74) *Attorney, Agent, or Firm* — K&L Gates LLP (57) ABSTRACT

A method of potentiating musculoskeletal effect of one or more anabolic amino acids in an individual in need thereof can include administering to the individual in need thereof a composition containing the one or more anabolic amino acids, the composition also containing one or more autophagy-inducing amino acids in a total amount effective for the composition to be at least neutral regarding autophagy. In another aspect, a method of overcoming one or more negative effects of one or more anabolic amino acids by preventing degenerative processes related to loss of autophagy can include administering to an individual in need thereof a composition containing the one or more anabolic amino acids, the composition further containing the one or more autophagy-inducing amino acids in a total amount effective for the composition to be at least neutral regarding autophagy.

18 Claims, 4 Drawing Sheets

COMPOSITIONS AND METHODS USING ONE OR MORE AUTOPHAGY-INDUCING AMINO ACIDS TO POTENTIATE MUSCULOSKELETAL EFFECT OF ONE OR MORE ANABOLIC AMINO ACIDS

CROSS REFERENCE TO RELATED APPLICATIONS

The present application is a National Stage of International Application No. PCT/EP2020/065534, filed on Jun. 4, 2020, which claims priority to U.S. Provisional Patent Application No. 62/858,496, filed on Jun. 7, 2019, the entire contents of which are being incorporated herein by reference.

BACKGROUND

The present disclosure generally relates to compositions and methods which use one or more autophagy-inducing amino acids, for example Glycine, Cysteine, Proline, Glutamate, Valine, Tyrosine or their precursors to potentiate the effect of one or more anabolic amino acids such as Leucine, Isoleucine, Arginine, Glutamine or Citrulline. More specifically, the present disclosure relates to administering a composition comprising one or more anabolic amino acids, the composition further comprising one or more autophagy-inducing amino acids or their precursors in an amount effective for the composition to be at least neutral regarding autophagy and preferably positive regarding autophagy, despite any negative effect on autophagy from the one or more anabolic amino acids. The composition can concomitantly promote protein synthesis and removal of damaged cellular materials. The recipient of administration can be a critically ill patient, for example a patient in the Intensive Care Unit (ICU); an ageing patient, for example an elderly individual; a patient with sarcopenia or frailty; or an individual with chronic kidney disease (e.g., with a loss of amino acids from dialysis) and/or acute kidney injury.

Due to major advances in intensive care medicine, critically ill patients often survive acute conditions that were previously lethal. Nevertheless, mortality remains high in these patients who survive this initial phase and enter a chronic phase of critical illness. Mortality is often from non-resolving multiple organ failure, acute kidney injury and failure, critical illness myopathy, or less severe forms of muscle weakness. Treatments have been introduced to improve muscle myopathy and weakness, such as hyperalimentation, growth hormone, or androgens, but have failed because these interventions unexpectedly increased the risk of organ failure and death. Moreover, the nutritional support to trauma and surgery patients may actually have detrimental effects.

Effective measures to provide critically ill patients with appropriate treatments and adequate nutrition remain lacking.

Moreover, age-related loss of muscle mass and function is inevitable in all individuals; however its progression largely depends on genetic and environmental factors such as physical activity and nutritional intake. Sarcopenia has been defined as the point where the age-related loss of muscle mass and function gets debilitating and impacts quality of life. In contrast, frailty is another classification of age-related physical function decline that features low muscle strength and functionality, but not muscle mass. Sarcopenia is defined clinically according to low muscle mass and function, using cutoffs which stratify the elderly population for individuals in a state of pathological mobility. Sarcopenia predicts future disability and mortality, and was assigned an official ICD-10 disease code in 2016 (Anker et al., 2016).

SUMMARY

The degradation of cytoplasmic proteins is mediated by a cellular process referred to as macroautophagy, also referred to simply as autophagy. Autophagy processes are also involved in the inflammatory response and facilitate immune system destruction of bacteria. Autophagy constitutes the major lysosomal degradation pathway recycling damaged and potentially harmful cellular material such as damaged mitochondria. Notably, autophagy counteracts cell death and prolongs life span in various ageing models.

As detailed in the experimental data set forth later herein, the inventors found that some amino acids that are known to be involved in musculoskeletal anabolism through the mTOR pathway, for example Arginine, Glutamine and Leucine, and/or anabolic branched-chain amino acids, for example Leucine and Isoleucine, reduce basal autophagy. However, the inventors discovered that some amino acids, such as Glycine, Cysteine, Proline, Glutamate, Valine, Tyrosine or their precursors such as Serine (as a precursor to Glycine), N-Acetyl Cysteine, and Methionine (as a precursor to Cysteine) can strongly induce autophagy and thus may counteract any negative impact from the anabolic amino acids on autophagy, including muscle and neuromuscular degeneration, and loss of muscle mass and function.

Accordingly, in a general embodiment, the present disclosure provides a method of potentiating musculoskeletal effect of one or more anabolic amino acids in an individual in need thereof. The method comprises administering to the individual a composition comprising the one or more anabolic amino acids, the composition further comprising one or more autophagy-inducing amino acids or their precursors in a total amount effective for the composition to be at least neutral regarding autophagy and preferably positive regarding autophagy.

In an embodiment, the one or more anabolic amino acids are selected from the group consisting of Leucine, Isoleucine, Arginine, Glutamine, Citrulline and mixtures thereof. The one or more anabolic amino acids can comprise at least one of Leucine, Glutamine or Arginine, in an amount effective to activate mTOR in the individual.

In an embodiment, the one or more autophagy-inducing amino acids are selected from the group consisting of Glycine, Cysteine, Proline, Glutamate, Valine, Tyrosine or their precursors and mixtures thereof.

In an embodiment, the composition induces autophagy in skeletal muscle.

In an embodiment, the individual is an ageing individual.

In an embodiment, the individual has sarcopenia or frailty or is at risk of developing sarcopenia or frailty.

In an embodiment, the individual is critically ill.

In an embodiment, the individual has critical illness myopathy or is at risk of developing critical illness myopathy.

In an embodiment, the individual has a critical illness with acute kidney failure or is at risk of developing acute kidney failure.

In an embodiment, the individual has a chronic kidney disease with or without related loss of muscle mass or function.

In an embodiment, the individual has cachexia or muscle wasting secondary to a chronic disease such as cancer, chronic obstructive pulmonary disease (COPD), chronic heart failure (CHF), acute kidney disease or chronic kidney disease (CKD).

In an embodiment, the composition comprises a protein that provides at least a portion of the one or more anabolic amino acids and/or at least a portion of the one or more autophagy-inducing amino acids or their precursors, the protein is selected from the group consisting of (i) protein from an animal source, (ii) protein from a plant source and (iii) a mixture thereof, preferably one or more of (a) milk protein, (b) whey protein, (c) caseinate, (d) micellar casein, (e) pea protein, (f) soy protein and (g) mixtures thereof. In a particular non-limiting example, at least a portion of the protein is collagen, i.e., unhydrolyzed and/or hydrolyzed collagen.

The protein can be selected from the group consisting of (i) free form amino acids, (ii) unhydrolyzed protein, (iii) partially hydrolyzed protein, (iv) extensively hydrolyzed protein, and (v) mixtures thereof. The protein can comprise peptides having a length of 2 to 10 amino acids. Optionally at least a portion of the protein is 5 to 95% hydrolyzed. Optionally the protein has a formulation selected from the group consisting of (i) at least 50% of the protein has a molecular weight of 1-5 kDa, (ii) at least 50% of the protein has a molecular weight of 5-10 kDa and (iii) at least 50% of the protein has a molecular weight of 10-20 kDa.

In an embodiment, the composition comprises a carbohydrate source and/or a fat source.

In an embodiment, the administering uses at least one route selected from the group of oral, enteral, parenteral and intravenous injection.

In an embodiment, the total amount of the one or more anabolic amino acids is approximately equal to or is greater than a total amount of the one or more anabolic amino acids in the composition.

In another embodiment, the present disclosure provides a composition comprising one or more anabolic amino acids, the composition further comprising one or more autophagy-inducing amino acids or their precursors in a total amount effective for the composition to be at least neutral regarding autophagy and preferably positive regarding autophagy. The composition can be selected from the group consisting of food compositions, dietary supplements, nutritional compositions, nutraceuticals, powdered nutritional products to be reconstituted in water or milk before consumption, food additives, medicaments, drinks, and combinations thereof.

In another embodiment, the present disclosure provides a method of making a therapeutic composition, the method comprising adding one or more autophagy-inducing amino acids or their precursors to a base composition comprising one or more anabolic amino acids to form the therapeutic composition, the one or more autophagy-inducing amino acids or their precursors are added to the base composition in an amount effective for the therapeutic composition to be at least neutral regarding autophagy and preferably positive regarding autophagy. The base composition and/or the therapeutic composition can be formulated for administration by at least one route selected from the group of oral, enteral, parenteral and intravenous injection. The base composition can be negative regarding autophagy induction (i.e., the composition is negative in total), and/or the base composition can be neutral or positive regarding autophagy induction but contain an amount of the one or more anabolic amino acids that is negative regarding autophagy induction (i.e., the one or more anabolic amino acids form a portion that is negative regarding autophagy induction).

In an embodiment, the method comprises quantifying a total amount of the one or more anabolic amino acids in the base composition; and using the total amount of the one or more anabolic amino acids in the base composition to determine the total amount of the one or more autophagy-inducing amino acids added to the base composition. The using of the total amount of the one or more anabolic amino acids in the base composition to determine the total amount of the one or more autophagy-inducing amino acids added to the base composition preferably comprises determining an expected effect on autophagy from the total amount of the one or more anabolic amino acids. The using of the total amount of the one or more anabolic amino acids in the base composition to determine the total amount of the one or more autophagy-inducing amino acids added to the base composition preferably further comprises determining the total amount of the one or more autophagy-inducing amino acids added to the base composition such that an expected effect on autophagy from the total amount of the one or more autophagy-inducing amino acids added to the base composition is approximately equal to or greater than the expected effect on autophagy from the total amount of the one or more anabolic amino acids.

In another embodiment, the present disclosure provides a method comprising administering an amount of a composition that concomitantly promotes protein synthesis and removal of damaged cellular materials to an individual in need thereof, the composition comprising one or more anabolic amino acids, the composition further comprising one or more autophagy-inducing amino acids or their precursors in a total amount effective for the composition to be at least neutral regarding autophagy and preferably positive regarding autophagy.

In another embodiment, the present disclosure provides a method of overcoming one or more negative effects of one or more anabolic amino acids by preventing degenerative processes related to loss of autophagy. The method comprises administering to an individual a composition comprising the one or more anabolic amino acids, the composition further comprising one or more autophagy-inducing amino acids or their precursors in an amount effective for the composition to be at least neutral regarding autophagy and preferably positive regarding autophagy, for example in muscle.

An advantage of one or more embodiments provided by the present disclosure is to improve the condition of critically ill animals, critically ill humans, ageing animals, or ageing humans.

Another advantage of one or more embodiments provided by the present disclosure is to prevent or treat excessive catabolism, e.g., in a critically ill patient or an ageing individual.

Still another advantage of one or more embodiments provided by the present disclosure is to reduce or prevent the risk of morbidity or mortality due to excessive catabolism, e.g., in a critically ill patient or an ageing individual.

An additional advantage of the present disclosure is to reverse, treat or cure multiple organ dysfunction syndrome in a critically ill patient.

An additional advantage of one or more embodiments provided by the present disclosure is to protect an ageing individual from neurological diseases, such as mild cognitive impairment, Alzheimer disease, Parkinson's disease, Amyloid Lateral Sclerosis, Multiple Sclerosis, Huntington disease, dementia, and related neurological orphan diseases.

An additional advantage of one or more embodiments provided by the present disclosure is to protect an ageing individual from muscle dysfunction, for example sarcopenia, frailty, inclusion body myositis, myopathy/myolysis induced by drugs such as corticosteroids or statins, muscle wasting induced by immobilization or hospitalization.

An additional advantage of one or more embodiments provided by the present disclosure is to protect a patient suffering from a genetic disease, including but not restricted to muscular dystrophies such as Duchenne Muscular Dystrophy or Collagen VI muscular dystrophy, mitochondrial encephalomyopathies, mitochondrial myopathies, glycogen storage diseases, lysosomal storage diseases, Pompe disease.

Another advantage of one or more embodiments provided by the present disclosure is a composition that can be administered parenterally or enterally, for example as an aqueous liquid composition, to a critically ill patient to induce autophagy, for example to treat multiple organ dysfunction or burn.

Yet another advantage of one or more embodiments provided by the present disclosure is to decrease a length of time that a critically ill patient spends on a ventilator or to accelerate the weaning time from a ventilator.

Another advantage of one or more embodiments provided by the present disclosure is to protect a critically ill patient subjected to parenteral nutrition, e.g., against multiple organ failure or muscle weakness caused by parenteral nutrient delivery, particularly unbalanced or relative nutrient overload.

An additional advantage of one or more embodiments provided by the present disclosure is to protect an ageing individual from muscle weakness.

Still another advantage of one or more embodiments provided by the present disclosure is to increase the survivability of a critically ill patient or an ageing individual.

An additional advantage of one or more embodiments provided by the present disclosure is to accelerate the regain of mobility, or shorten the time of immobility, after discharge from the intensive care unit.

Yet another advantage of one or more embodiments provided by the present disclosure is a beneficial effect even when a critically ill patient is already at a far-developed stage of a life threatening condition.

Additional features and advantages are described in, and will be apparent from, the following Detailed Description and the Figures.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

All percentages are by weight of the total weight of the composition unless expressed otherwise. Similarly, all amounts and all ratios are by weight unless expressed otherwise. When reference is made to the pH, values correspond to pH measured at 25° C. with standard equipment. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used herein and in the appended claims, the singular form of a word includes the plural, unless the context clearly dictates otherwise. Thus, the references "a," "an" and "the" are generally inclusive of the plurals of the respective terms. For example, reference to "an amino acid" or "the amino acid" includes a plurality of such "amino acids." The term "and/or" used in the context of "X and/or Y" should be interpreted as "X," or "Y," or "X and Y." Similarly, "at least one of X or Y" should be interpreted as "X," or "Y," or "both X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of" and "consisting of" the disclosed components.

Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

"Animal" includes, but is not limited to, mammals, which includes but is not limited to rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage, e.g., an animal capable of autophagy. As used herein, the term "patient" is understood to include an animal, for example a mammal, and preferably a human that is receiving or intended to receive treatment, as treatment is herein defined. While the terms "individual" and "patient" are often used herein to refer to a human, the present disclosure is not so limited.

Accordingly, the terms "individual" and "patient" refer to any animal, mammal or human that can benefit from the methods and compositions disclosed herein. Indeed, nonhuman animals undergo prolonged critical illness that mimics the human condition. These critically ill animals undergo the same metabolic, immunological and endocrine disturbances and development of organ failure and muscle wasting as the human counterpart. Moreover, animals experience the effects of ageing as well.

The term "elderly" in the context of a human means an age from birth of at least 55 years, preferably above 63 years, more preferably above 65 years, and most preferably above 70 years. The term "older adult" or "ageing individual" in the context of a human means an age from birth of at least 45 years, preferably above 50 years, more preferably above 55 years, and includes elderly individuals.

For other animals, an "older adult" or "ageing individual" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An ageing cat or dog has an age from birth of at least about 5 years. An elderly cat or dog has an age from birth of at least about 7 years.

"Sarcopenia" is defined as the age-associated loss of muscle mass and functionality (including muscle strength and gait speed). Sarcopenia can be characterized by one or more of low muscle mass, low muscle strength and low physical performance.

Low muscle mass can generally be based on low appendicular lean mass normalized to height square (ALM index), particularly ALM index less than 7.00 kg/m2 for men and 5.40 kg/m2 for women. Low physical performance can generally be based on gait speed, particularly gait speed of <0.8 m/sec. Low muscle strength can generally be based on low hand grip strength, particularly hand grip strength less than 26 kg in men and less than 18 kg in women.

Additionally or alternatively, sarcopenia can be diagnosed in a subject based on the definition of the EWGSOP (European Working Group for Sarcopenia in Older People), for example as described in Crutz-Jentoft et al., 2010. Low muscle mass can generally be based on low appendicular lean mass normalized to height square (ALM index), particularly ALM index less than 7.23 kg/m2 for men and 5.67 kg/m2 for women. Low physical performance can generally be based on gait speed, particularly gait speed of <0.8 m/sec. Low muscle strength can generally be based on low hand grip strength, particularly hand grip strength less than 30 kg in men and less than 20 kg in women.

Additionally or alternatively, sarcopenia can be diagnosed in a subject based on the definition of the Foundation for the National Institutes of Health (FNIH), for example as described in Studenski et al., 2014. Low muscle mass can generally be based on low appendicular lean mass (ALM) normalized to body mass index (BMI; kg/m2), particularly ALM to BMI less than 0.789 for men and 0.512 for women. Low physical performance can generally be based on gait speed, particularly gait speed of <0.8 m/sec. Low muscle strength can generally be based on low hand grip strength, particularly hand grip strength less than 26 kg in men and less than 16 kg in women. Low muscle strength can also generally be based on low hand grip strength to body mass index, particularly hand grip strength to body mass index less than 1.00 in men and less than 0.56 in women.

As used herein, "frailty" is defined as a clinically recognizable state of increased vulnerability resulting from aging-associated decline in reserve and function across multiple physiologic systems such that the ability to cope with everyday or acute stressors is compromised. In the absence of an established quantitative standard, frailty has been operationally defined by Fried et al. as meeting three out of five phenotypic criteria indicating compromised energetics: (1) weakness (grip strength in the lowest 20% of population at baseline, adjusted for gender and body mass index), (2) poor endurance and energy (self-reported exhaustion associated with $VO_2$ max), (3) slowness (lowest 20% of population at baseline, based on time to walk 15 feet, adjusting for gender and standing height), (4) low physical activity (weighted score of kilocalories expended per week at baseline, lowest quintile of physical activity identified for each gender; e.g., less than 383 kcal/week for males and less than 270 kcal/week for females), and/or unintentional weight loss (10 lbs. in past year). Fried L P, Tangen C M, Walston J, et al., "Frailty in older adults: evidence for a phenotype." J. Gerontol. A. Biol. Sci. Med. Sci. 56(3):M146-M156 (2001). A pre-frail stage, in which one or two of these criteria are present, identifies a high risk of progressing to frailty.

"Cachexia" is a complex metabolic syndrome associated with underlying illness and characterized by loss of muscle with or without loss of fat mass. The prominent clinical feature of cachexia is weight loss in adults (corrected for fluid retention) or growth failure in children (excluding endocrine disorders).

Cachexia is often seen in patients with diseases such as cancer, chronic heart failure, renal failure, chronic obstructive pulmonary disease, AIDS, autoimmune disorders, chronic inflammatory disorders, cirrhosis of the liver, anorexia, chronic pancreatitis and/or metabolic acidosis and neurodegenerative disease.

There are certain types of cancer wherein cachexia is particularly prevalent, for example, pancreas, esophagus, stomach, bowel, lung and/or liver cancer.

The internationally recognized diagnostic criterion for cachexia is weight loss greater than 5% over a restricted time, for example 6 months, or weight loss greater than 2% in individuals already showing depletion according to current body weight and height (body-mass index [BMI] <20 kg/m$^2$) or skeletal muscle mass (measured by DXA, MRI, CT or bioimpedance). Cachexia can develop progressively through various stages—precachexia to cachexia to refractory cachexia. Severity can be classified according to degree of depletion of energy stores and body protein (BMI) in combination with degree of ongoing weight loss.

In particular, cancer cachexia has been defined as weight loss >5% over past 6 months (in absence of simple starvation); or BMI <20 and any degree of weight loss >2%; or appendicular lean mass consistent with low muscle mass (males <7.26 kg/m$^2$; females <5.45 kg/m$^2$) and any degree of weight loss >2% (Fearon et al. 2011).

"Precachexia" may be defined as weight loss ≤5% together with anorexia and metabolic change. At present there are no robust biomarkers to identify those precachectic patients who are likely to progress further or the rate at which they will do so. Refractory cachexia is defined essentially on the basis of the patient's clinical characteristics and circumstances.

The terms "treatment" and "treating" include any effect that results in the improvement of the condition or disorder, for example lessening, reducing, modulating, or eliminating the condition or disorder. The term does not necessarily imply that a subject is treated until total recovery. Non-limiting examples of "treating" or "treatment of" a condition or disorder include: (1) inhibiting the condition or disorder, i.e., arresting the development of the condition or disorder or its clinical symptoms and (2) relieving the condition or disorder, i.e., causing the temporary or permanent regression of the condition or disorder or its clinical symptoms. A treatment can be patient- or doctor-related.

The terms "prevention" or "preventing" mean causing the clinical symptoms of the referenced condition or disorder to not develop in an individual that may be exposed or predisposed to the condition or disorder but does not yet experience or display symptoms of the condition or disorder. The terms "condition" and "disorder" mean any disease, condition, symptom, or indication.

The relative terms "improved," "increased," "enhanced" and the like refer to the effects of the composition comprising both one or more anabolic amino acids and one or more autophagy-inducing amino acids relative to a composition without the one or more autophagy-inducing amino acids or with less of the one or more autophagy-inducing amino acids, but otherwise identical.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the essential elements and limitations described herein, as well as any additional or optional ingredients, components, or limitations described herein or otherwise useful in a diet.

As used herein, "complete nutrition" contains sufficient types and levels of macronutrients (protein, fats and carbohydrates) and micronutrients to be sufficient to be a sole source of nutrition for the animal to which the composition is administered. Individuals can receive 100% of their nutritional requirements from such complete nutritional compositions.

As used herein, the term "critically ill patient" is an individual experiencing an acute life-threatening episode or diagnosed to be in imminent danger of such an episode. A critically ill patient is medically unstable and, when not treated, likely to die (e.g., >50% chance of death).

Non-limiting examples of critically ill patients include a patient who has sustained or is at risk of sustaining acutely life-threatening single or multiple organ system failure due to disease or injury, a patient who is being operated upon and where complications supervene, and a patient who has a vital organ operated upon within the last week or who has been subject to major surgery within the last week.

More specific non-limiting examples of a critically ill patient include a patient who has sustained or is at risk of sustaining acutely life-threatening single or multiple organ system failure due to disease or injury and a patient who is being operated upon and where complications supervene. Additional specific non-limiting examples of a critically ill patient include a patient in need of one or more of cardiac surgery, cerebral surgery, thoracic surgery, abdominal surgery, vascular surgery, or transplantation; and a patient suffering from one or more of a neurological disease, cerebral trauma, respiratory insufficiency, abdominal peritonitis, multiple trauma, a severe burn, or critical illness polyneuropathy.

The term "Intensive Care Unit" (ICU) refers to the part of a hospital where critically ill patients are treated. The term "Intensive Care Unit" also covers a nursing home; a clinic, for example, a private clinic; or the like if the treatment activities performed there are the same or similar as those of an ICU. An "ICU patient" is encompassed by the term "critically ill patient."

The term "multiple organ dysfunction" refers to a condition resulting from infection, hypoperfusion, hypermetabolism or injury such as accident or surgery. The "multiple organ failure" of which critically ill patients die is considered a descriptive clinical syndrome defined by a dysfunction or failure of at least two vital organ systems. The vital organ systems that are uniformly and most specifically affected are the liver, the kidneys, the lungs, as well as the cardiovascular system, the nervous system and the hematological system. Non-limiting examples of multiple organ dysfunction include acute respiratory distress syndrome, heart failure, liver failure, renal failure, respiratory insufficiency, intensive care, shock, extensive burns, sepsis (e.g., systemic inflammatory response syndrome) and stroke.

The term "enterally administering" encompasses oral administration (including oral gavage administration), as well as rectal administration, although oral administration is preferred. The term "parenterally administering" refers to delivery of substances given by routes other than the digestive tract and covers administration routes such as intravenous, intra-arterial, intramuscular, intracerebroventricular, intraosseous, intradermal, intrathecal, and also intraperitoneal administration, intravesical infusion and intracavernosal injection.

Preferred parenteral administration is intravenous administration. A particular form of parenteral administration is delivery by intravenous administration of nutrition. Parenteral nutrition is "total parenteral nutrition" when no food is given by other routes. "Parenteral nutrition" is preferably a isotonic or hypertonic aqueous solution (or solid compositions to be dissolved, or liquid concentrates to be diluted to obtain an isotonic or hypertonic solution) comprising a saccharide such as glucose and further comprising one or more of lipids, amino acids, and vitamins.

Embodiments

An aspect of the present disclosure is a method of potentiating musculoskeletal effect of one or more anabolic amino acids in an individual in need thereof. The method comprises administering to the individual a composition comprising the one or more anabolic amino acids, the composition further comprising one or more autophagy-inducing amino acids or their precursors in an amount effective for the composition to be at least neutral regarding autophagy and preferably positive regarding autophagy, for example in muscle. The composition can be administered parenterally, enterally, or intravenously. The one or more anabolic amino acids are different compounds than the one or more autophagy-inducing amino acids.

As used herein, "potentiating musculoskeletal effect" means (i) the positive (anabolic) effects of the one or more anabolic amino acids are greater than if the one or more autophagy-inducing amino acids were completely absent or present in a lower amount in an otherwise identically formulated composition and/or (ii) the positive (anabolic) effects of the one or more anabolic amino acids last longer than if the one or more autophagy-inducing amino acids were completely absent or present in a lower amount in an otherwise identically formulated composition.

Non-limiting examples of suitable anabolic amino acids include Leucine, Isoleucine, Arginine, Glutamine, Citrulline and mixtures thereof. The composition can comprise one or more of Leucine, Isoleucine or Arginine, in free form and/or bound as peptides and/or proteins such as dairy, animal or plant proteins. Preferably any Leucine or Arginine is present in the composition in an amount effective to activate mTOR. A daily dose of the composition can include one or more of 0.175-142.85 mg/kg bw Leucine, preferably 0.35-71.425 mg/kg bw Leucine; 0.175-71.425 mg/kg bw Isoleucine; 20-300 mg/kg bw Arginine, preferably 50-200 mg/kg bw Arginine and/or 20-300 mg/kg bw Citrulline, preferably 100-200 mg/kg bw Citrulline. The daily dose of the one or more anabolic amino acids can be provided by one or more servings of the composition per day.

Non-limiting examples of suitable autophagy-inducing amino acids include Glycine, Cysteine, Proline, Glutamate, Valine, Tyrosine or their precursors such as Serine (as a precursor to Glycine), N-Acetyl Cysteine, Methionine (as a precursor to Cysteine) and mixtures thereof. The composition comprises the one or more autophagy-inducing amino acids or their precursors in an amount effective for the composition to be at least neutral regarding autophagy and preferably positive regarding autophagy despite any negative effect on autophagy from the one or more anabolic amino acids.

Whey protein is rich in BCAAs such as Leucine and Isoleucine. Therefore, some embodiments of the composition comprise whey protein that provides at least a portion of the anabolic amino acids in the composition. Moreover, hydrolyzed collagen is a rich source of glycine and proline, and thus some embodiments of the composition comprise autophagy-inducing amino acids that provides at least a portion of the anabolic amino acids in the composition.

The composition can induce autophagy in muscle, for example a skeletal muscle. Non-limiting examples of such muscle include one or more of the following: vastus lateralis, gastrocnemius, tibialis, soleus, extensor, digitorum longus (EDL), biceps femoris, semitendinosus, semimembranosus, gluteus maximus, extra-ocular muscles, face muscles or diaphragm.

The individual in need of induced autophagy can be an ageing individual, such as an ageing animal or an ageing human. In some embodiments, the individual in need of induced autophagy is an elderly animal or an elderly human.

The individual in need of induced autophagy can be a critically ill patient. In various embodiments, the method can treat or prevent multiple organ dysfunction in the critically ill patient, e.g., if the patient has failed or disturbed homeostasis from receiving parenteral nutrition; can protect the critically ill patient against multiple organ dysfunction; can treat or prevent development of lactic acidosis, for example lactic acidosis induced by parenteral nutrition; can treat or prevent muscle weakening in the critically ill patient; can decrease or prevent morbidity or mortality nutrition aggravated by parenteral nutrition; and/or can prevent body system collapse.

In some embodiments, the critically ill patient has at least one life threatening condition selected from the group consisting of lactic acidosis, muscle weakening, hyperglycemia, multiple organ failure, failed homeostasis, and disturbed homeostasis. In an embodiment, the critically ill patient has a non-infectious disorder. In an embodiment, the critically ill patient has multiple organ dysfunction that is not caused or associated with sepsis. Multiple organ dysfunction and muscle weakness are common in the critical care setting and can be caused or aggravated by unbalanced parenteral nutrient delivery or a parenterally delivered relative or absolute nutrient overload.

In some embodiments, the critically ill patient has at least one disorder selected from the group consisting of severe trauma, multiple trauma, high risk surgery, extensive surgery, cerebral trauma, cerebral bleeding, respiratory insufficiency, abdominal peritonitis, acute kidney injury, acute liver injury, severe burns, critical illness polyneuropathy, critical illness myopathy, and ICU-acquired muscle weakness.

In some embodiments, the critically ill patient is receiving enteral or parenteral nutrition. In some embodiments, the composition treats or prevents mitochondrial dysfunction, for example mitochondrial dysfunction induced by inadequate or unbalanced parenteral nutrition to a critically ill patient.

In another aspect of the present disclosure, a method overcomes one or more negative effects of one or more anabolic amino acids by preventing degenerative processes related to loss of autophagy. The method comprises administering to an individual a composition comprising the one or more anabolic amino acids, the composition further comprising one or more autophagy-inducing amino acids or their precursors in an amount effective for the composition to be at least neutral regarding autophagy and preferably positive regarding autophagy, for example in muscle.

The term "protein" as used herein includes free form amino acids, molecules between 2 and 20 amino acids (referenced herein as "peptides"), and also includes longer chains of amino acids as well. Small peptides, i.e., chains of 2 to 10 amino acids, are suitable for the composition alone or in combination with other proteins. The "free form" of an amino acid is the monomeric form of the amino acid. Suitable amino acids include both natural and non-natural amino acids. The composition can comprise a mixture of one or more types of protein, for example one or more (i) peptides, (ii) longer chains of amino acids, or (iii) free form amino acids; and the mixture is preferably formulated to achieve a desired amino acid profile/content.

The composition can comprise a protein that provides at least a portion of the one or more anabolic amino acids and/or at least a portion of the one or more autophagy-inducing amino acids, and at least a portion of the protein can be from animal or plant origin, for example dairy protein such as one or more of milk protein, e.g., milk protein concentrate or milk protein isolate; caseinates or casein, e.g., micellar casein concentrate or micellar casein isolate; or whey protein, e.g., whey protein concentrate or whey protein isolate. Additionally or alternatively, at least a portion of the protein can be plant protein such as one or more of soy protein or pea protein.

Mixtures of these proteins are also suitable, for example mixtures in which casein is the majority of the protein but not the entirety, mixtures in which whey protein is the majority of the protein but not the entirety, mixtures in which pea protein is the majority of the protein but not the entirety, and mixtures in which soy protein is the majority of the protein but not the entirety. In an embodiment, at least 10 wt. % of the protein is whey protein, preferably at least 20 wt. %, and more preferably at least 30 wt. %. In an embodiment, at least 10 wt. % of the protein is casein, preferably at least 20 wt. %, and more preferably at least 30 wt. %. In an embodiment, at least 10 wt. % of the protein is plant protein, preferably at least 20 wt. %, more preferably at least 30 wt. %.

Whey protein may be any whey protein, for example selected from the group consisting of whey protein concentrates, whey protein isolates, whey protein micelles, whey protein hydrolysates, acid whey, sweet whey, modified sweet whey (sweet whey from which the caseino-glycomacropeptide has been removed), a fraction of whey protein, and any combination thereof.

Casein may be obtained from any mammal but is preferably obtained from cow milk and preferably as micellar casein.

The protein may be unhydrolyzed, partially hydrolyzed (i.e., peptides of molecular weight 3 kDa to 10 kDa with an average molecular weight less than 5 kDa) or extensively hydrolyzed (i.e., peptides of which 90% have a molecular weight less than 3 kDa), for example in a range of 5% to 95% hydrolyzed. In some embodiments, the peptide profile of hydrolyzed protein can be within a range of distinct molecular weights. For example, the majority of peptides (>50 molar percent or >50 wt. %) can have a molecular weight within 1-5 kDa, or 5-10 kDa, or 10-20 kDa.

In an embodiment, the composition includes a source of carbohydrates. Any suitable carbohydrate may be used in the composition including, but not limited to, starch (e.g., modified starch, amylose starch, tapioca starch, corn starch), sucrose, lactose, glucose, fructose, corn syrup solids, maltodextrin, xylitol, sorbitol or combinations thereof.

The source of carbohydrates is preferably not greater than 50 energy % of the composition, more preferably not greater than 36 energy % of the composition, and most preferably not greater than 30 energy % of the composition.

In an embodiment, the composition includes a source of fat. The source of fat may include any suitable fat or fat mixture. Non-limiting examples of suitable fat sources include vegetable fat, such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like, animal fats such as milk fat; or combinations thereof.

The composition can be administered to an individual such as a human, e.g., an ageing individual or a critically ill individual, in a therapeutically effective dose. The therapeutically effective dose can be determined by the person skilled in the art and will depend on a number of factors known to those of skill in the art, such as the severity of the condition and the weight and general state of the individual.

The composition is preferably administered to the individual at least two days per week, more preferably at least three days per week, most preferably all seven days of the week; for at least one week, at least one month, at least two months, at least three months, at least six months, or even longer. In some embodiments, the composition is administered to the individual consecutively for a number of days, for example at least until a therapeutic effect is achieved. In an embodiment, the composition can be administered to the individual daily for at least 30, 60 or 90 consecutive days.

The above examples of administration do not require continuous daily administration with no interruptions. Instead, there may be some short breaks in the administration, such as a break of two to four days during the period of administration. The ideal duration of the administration of the composition can be determined by those of skill in the art.

In a preferred embodiment, the composition is administered to the individual orally or enterally (e.g. tube feeding). For example, the composition can be administered to the individual as a beverage, a capsule, a tablet, a powder or a suspension.

The composition can be any kind of composition that is suitable for human and/or animal consumption. For example, the composition may be selected from the group consisting of food compositions, dietary supplements, nutritional compositions, nutraceuticals, powdered nutritional products to be reconstituted in water or milk before consumption, food additives, medicaments, beverages and drinks. In an embodiment, the composition is an oral nutritional supplement (ONS), a complete nutritional formula, a pharmaceutical, a medical or a food product. In a preferred embodiment, the composition is administered to the individual as a beverage. The composition may be stored in a sachet as a powder and then suspended in a liquid such as water for use.

In some instances where oral or enteral administration is not possible or not advised, the composition may also be administered parenterally.

In some embodiments, the composition is administered to the individual in a single dosage form, i.e. all compounds are present in one product to be given to an individual in combination with a meal. In other embodiments, the composition is co-administered in separate dosage forms, for example at least one component separately from one or more of the other components of the composition.

In another embodiment, the present disclosure provides a method of making a therapeutic composition, the method comprising adding one or more autophagy-inducing amino acids or their precursors to a base composition comprising one or more anabolic amino acids to form the therapeutic composition, the one or more autophagy-inducing amino acids or their precursors are added to the base composition in an amount effective for the therapeutic composition to be at least neutral regarding autophagy and preferably positive regarding autophagy. The base composition and/or the therapeutic composition can be formulated for administration by at least one route selected from the group of oral, enteral, parenteral and intravenous injection. The base composition can be negative regarding autophagy induction (i.e., the composition is negative in total), and/or the base composition can be neutral or positive regarding autophagy induction but contain an amount of the one or more anabolic amino acids that is negative regarding autophagy induction (i.e., the one or more anabolic amino acids form a portion that is negative regarding autophagy induction).

In an embodiment, the method comprises quantifying a total amount of the one or more anabolic amino acids in the base composition; and using the total amount of the one or more anabolic amino acids in the base composition to determine the total amount of the one or more autophagy-inducing amino acids added to the base composition. The using of the total amount of the one or more anabolic amino acids in the base composition to determine the total amount of the one or more autophagy-inducing amino acids added to the base composition preferably comprises determining an expected effect on autophagy from the total amount of the one or more anabolic amino acids. The using of the total amount of the one or more anabolic amino acids in the base composition to determine the total amount of the one or more autophagy-inducing amino acids added to the base composition preferably further comprises determining the total amount of the one or more autophagy-inducing amino acids added to the base composition such that an expected effect on autophagy from the total amount of the one or more autophagy-inducing amino acids added to the base composition is approximately equal to or greater than the expected effect on autophagy from the total amount of the one or more anabolic amino acids.

EXAMPLES

The following non-limiting examples present scientific data developing and supporting the concept of administering a composition comprising one or more anabolic amino acids, the composition further comprising one or more autophagy-inducing amino acids in an amount effective for the composition to be at least neutral regarding autophagy and preferably positive regarding autophagy, despite any negative effect on autophagy from the one or more anabolic amino acids, to thereby induce autophagy in an individual in need thereof.

Example 1

Experimental Protocol

A zebrafish autophagy reporter has been generated by stable expression of the LC3 protein fused to ZsGreen under the control of a skeletal muscle specific promoter. Larvae from outcrossed transgenic zebrafish have been raised at 28° C. under standard laboratory conditions and have been treated at 48 h post-fertilization in 96 well plates with the indicated amino acids at concentrations ranging from 0.25 to 10 mM (n=24). After 16 hours of treatment larvae were anesthetized with 0.016% tricaine and imaged with ImageXpress confocal system at 20× magnification (Molecular Devices). Z stack images were captured for each larva and maximal projection images were produced. Number of LC3 punctae have been calculated with MetaXpress software (Moleculare Devices) and normalized by fish area.

Figure 1:
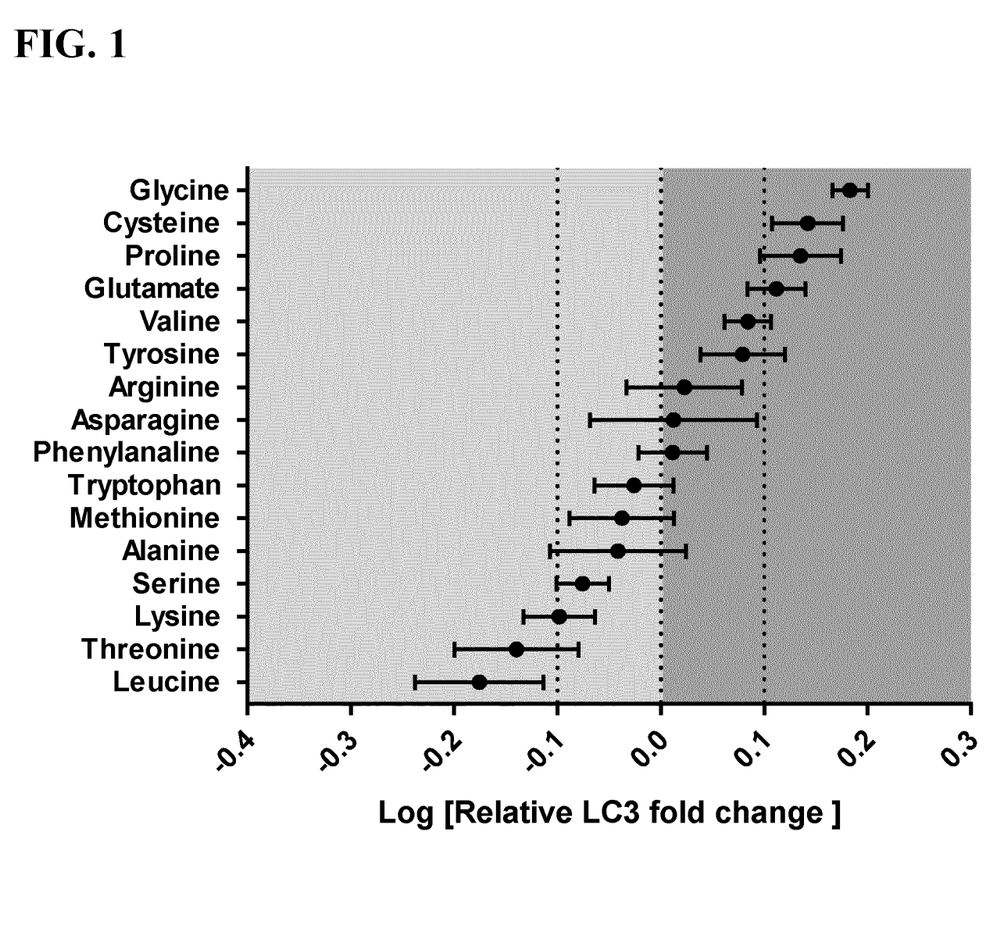
FIGS. 1-3 show autophagy activation by individual amino acids in the experimental example disclosed herein.
Figure 2:
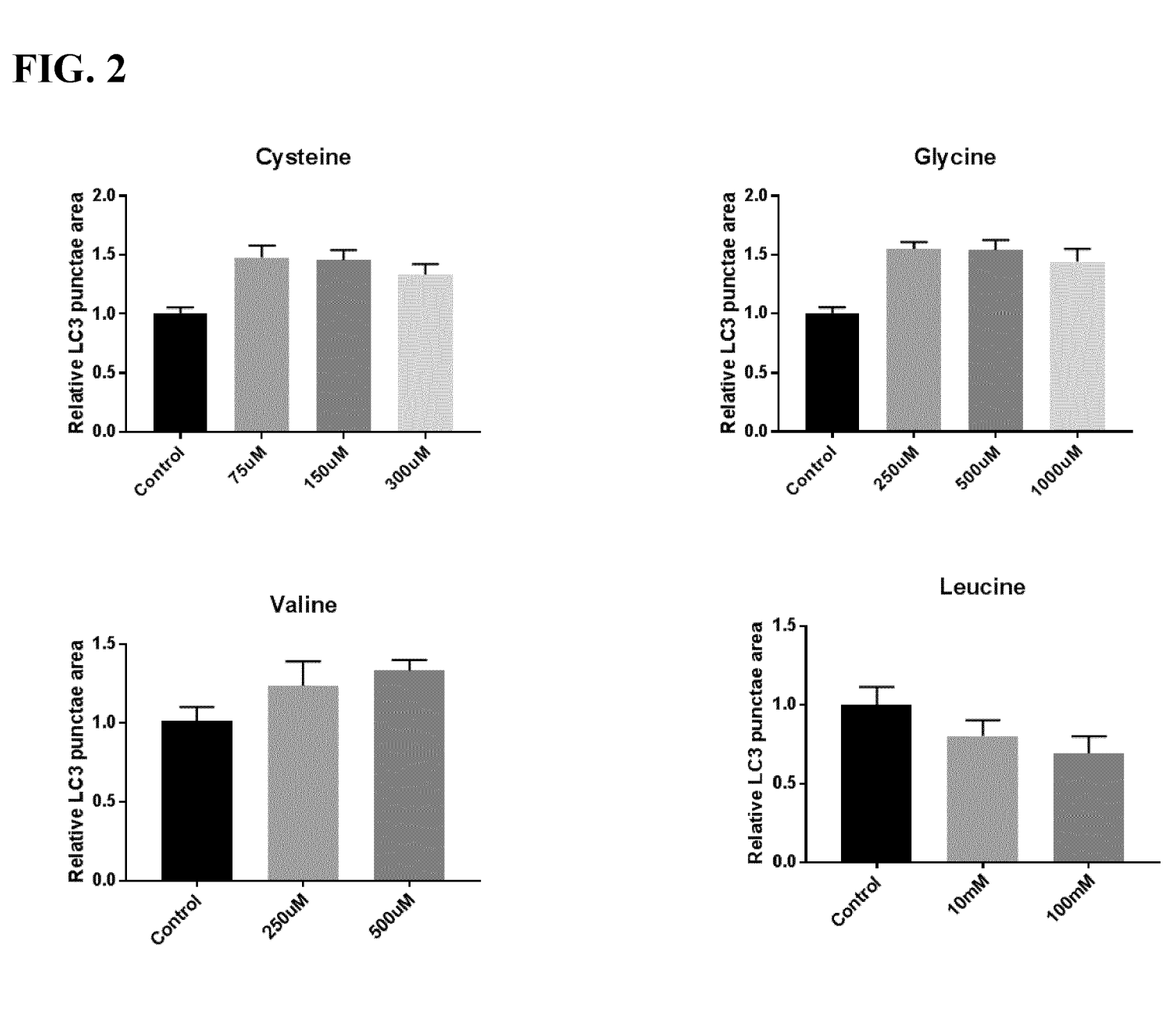
Figure 3:
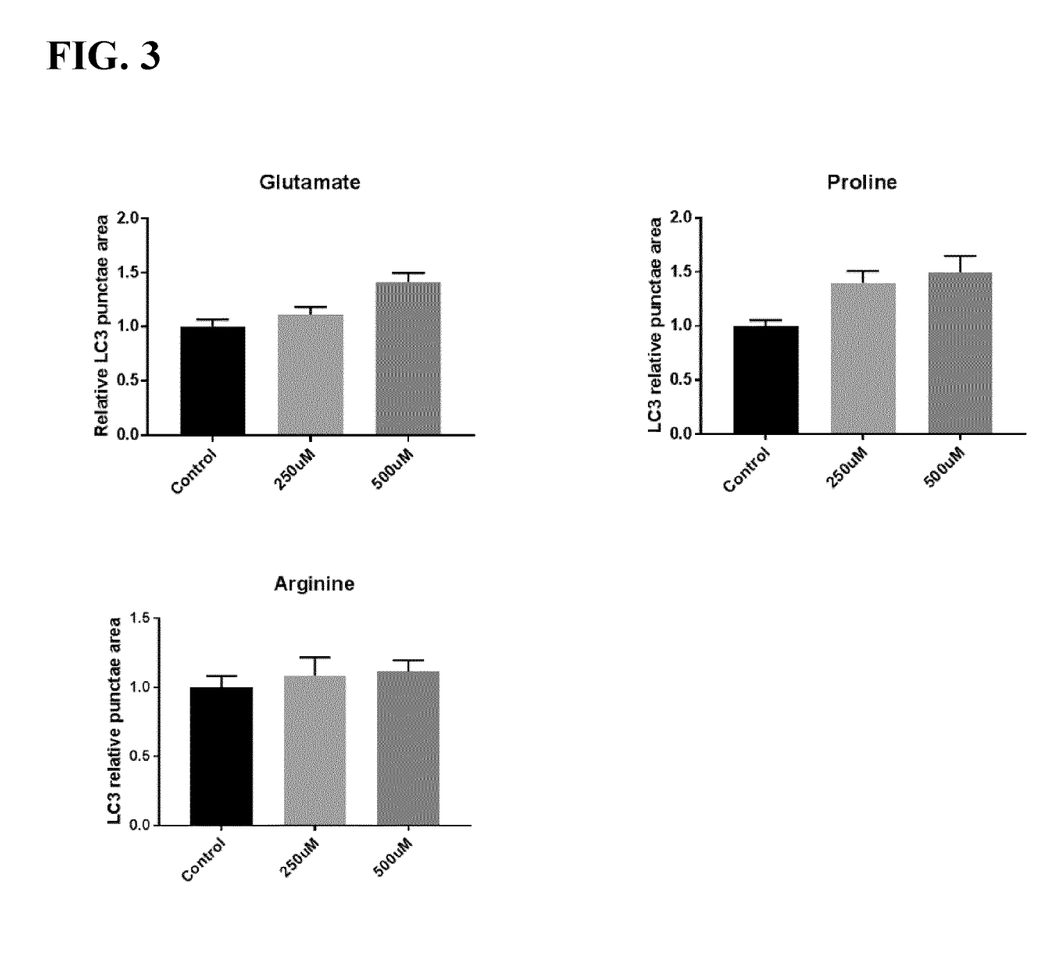

FIGS. 1-3 show the experimental results.

Example 2

Materials and Methods

Old mice are a good model to assess the effect of nutritional intervention in age-related decline. With this model, it can be observed as in human a decrease in muscle function with age. In this model, 20 months-old mice were fed for 3 months either with a normal diet or with the same diet supplemented with a specific amino acids mix (AAs) (see Table 1). The AAs mix dosage was 1.65 mg/kg BW/day.

TABLE 1

| Amino acid | % in the mix |
| --- | --- |
| Leucine | 28.67 |
| Isoleucine | 14.29 |
| Valine | 14.29 |
| Proline | 12.21 |
| Glycine | 12.21 |
| Lysine | 14.84 |
| Cysteine | 3.48 |

Figure 4:
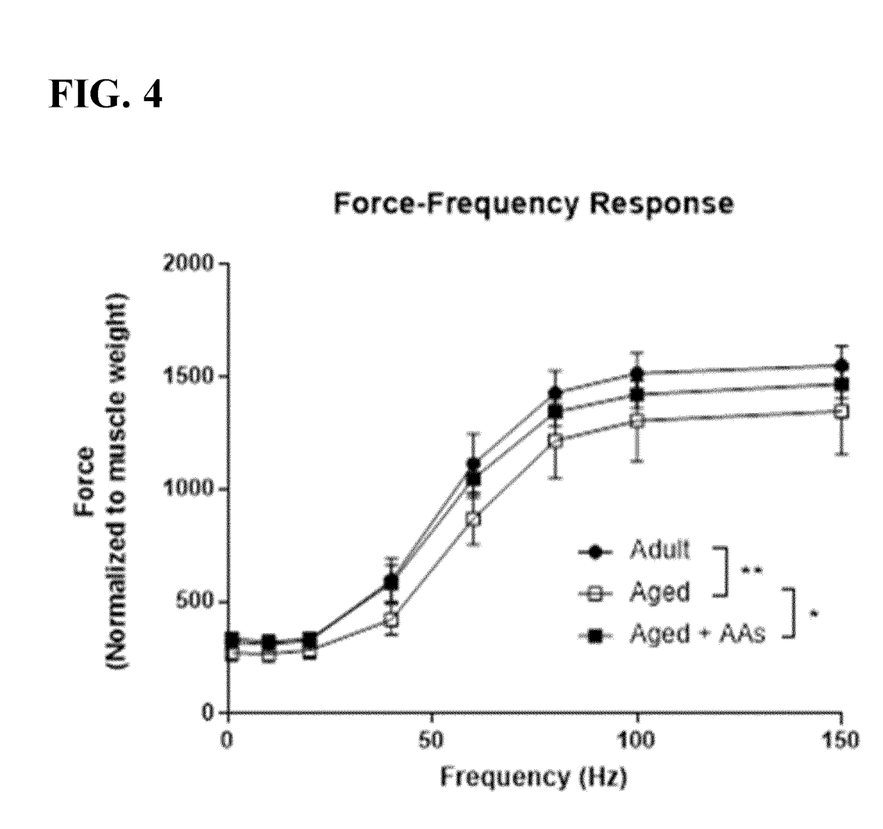
FIG. 4 shows the effect of a specific amino acid mix (AAs) on force frequency response in old rats (Aged) and the comparison with adult mice fed with a normal diet. 20 months-old rats were fed either a control diet or the same diet supplemented with a specific amino acids mix for 3 months. 6 months-old adult mice were fed a control diet for 3 months. Results were expressed as mean±S.E.M. Adult: 6 months-old mice fed a control diet. Aged: 20 months-old fed a control diet. Aged+AAs: 20 months-old fed a control diet supplemented with a specific amino acids mix.

In order to assess the effect of aging, adult mice (6 months old) were also fed for 3 months with a normal diet. The age related loss of in vivo force frequency response measured with a 305 C muscle lever system. FIG. 4, shows the effect of specific amino acid mix (AAs) on force frequency response in old rats (Aged) and the comparison with adult mice fed with a normal diet, said force frequency response was significantly improved with AAs supplementation suggesting an improvement in muscle function.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is as follows:

1. A method of potentiating a musculoskeletal effect of one or more anabolic amino acids selected from the group consisting of Leucine, Isoleucine, Arginine, Glutamine, Citrulline and mixtures thereof in an individual in need thereof, the method comprising administering to the individual a composition comprising the one or more anabolic amino acids, the composition further comprising one or more autophagy-inducing amino acids in a total amount effective for the composition to be neutral or positive regarding autophagy, the one or more autophagy-inducing amino acids comprising (i) Proline; and (ii) at least one additional amino acid selected from the group consisting of Glycine, Cysteine, Valine, Serine, N-Acetyl Cysteine (NAC), Methionine and mixtures thereof,
wherein the composition further comprises protein that provides at least a portion of the one or more anabolic amino acids and/or at least a portion of the one or more autophagy-inducing amino acids, and
wherein the protein has a formulation selected from the group consisting of (i) at least 50% of the protein has a molecular weight of 1-5 kDa, (ii) at least 50% of the protein has a molecular weight of 5-10 kDa and (iii) at least 50% of the protein has a molecular weight of 10-20 kDa.

2. The method of claim 1, wherein the one or more anabolic amino acids comprise at least one amino acid selected from the group consisting of Leucine, Arginine and Glutamine, in an amount effective to activate mTOR in the individual.

3. The method of claim 1, wherein the composition induces autophagy in skeletal muscle.

4. The method of claim 1, wherein the individual is an ageing individual.

5. The method of claim 1, wherein the individual has sarcopenia or frailty.

6. The method of claim 1, wherein the individual has at least one condition selected from the group consisting of (i) critically ill, (ii) acute kidney injury, (iii) chronic kidney injury, (iv) loss of muscle mass from chronic kidney disease, and (v) loss of muscle function from chronic kidney disease.

7. The method of claim 1, wherein the individual has a critical illness myopathy.

8. The method of claim 1, wherein the individual has cachexia or muscle wasting secondary to a chronic disease.

9. The method of claim 1, wherein at least a portion of the protein is selected from the group consisting of (i) protein from an animal source, (ii) protein from a plant source and (iii) a mixture thereof.

10. The method of claim 9, wherein at least a portion of the protein is selected from the group consisting of (i) milk protein, (ii) whey protein, (iii) caseinate, (iv) micellar casein, (v) pea protein, (vi) soy protein and (vii) mixtures thereof.

11. The method of claim 9, wherein at least a portion of the protein is selected from the group consisting of (i) free form amino acids, (ii) unhydrolyzed protein, (iii) partially hydrolyzed protein, (iv) extensively hydrolyzed protein, and (v) mixtures thereof.

12. The method of claim 9, wherein at least a portion of the protein is 5 to 95% hydrolyzed.

13. The method of claim 9, wherein the protein comprises peptides having a length of 2 to 10 amino acids.

14. The method of claim 1, wherein the composition comprises a carbohydrate source and/or a fat source.

15. The method of claim 1, wherein the administering uses at least one route selected from the group consisting of oral, enteral, parenteral and intravenous injection.

16. The method of claim 1, wherein the total amount of the one or more autophagy-inducing amino acids is approximately equal to or is greater than a total amount of the one or more anabolic amino acids in the composition.

17. The method of claim 1, wherein the one or more autophagy-inducing amino acids comprise Proline, Valine, Glycine and Cysteine.

18. The method of claim 17, wherein the one or more anabolic amino acids comprise Lysine, Leucine and Isoleucine.

* * * * *